US005667791A

United States Patent [19]

Hersh et al.

[11] Patent Number: 5,667,791
[45] Date of Patent: Sep. 16, 1997

[54] X-RAY INDUCED SKIN DAMAGE PROTECTIVE COMPOSITION

[75] Inventors: Theodore Hersh, Atlanta; Michael A. Warshaw, Savannah, both of Ga.

[73] Assignee: Thione INternational, Inc.

[21] Appl. No.: 658,105

[22] Filed: May 31, 1996

[51] Int. Cl.$^6$ ............................................. A61K 7/48
[52] U.S. Cl. .................. 424/401; 514/844; 514/937; 514/944
[58] Field of Search ................. 424/401; 514/844, 514/937, 944

[56] References Cited

U.S. PATENT DOCUMENTS

| | | | |
|---|---|---|---|
| 4,129,644 | 12/1978 | Kalopissis et al. | 424/59 |
| 4,144,325 | 3/1979 | Voyt | 424/59 |
| 4,224,339 | 9/1980 | Van Scott et al. | 424/289 |
| 4,567,200 | 1/1986 | Tinti et al. | 514/547 |
| 4,593,043 | 6/1986 | Tinti et al. | 514/547 |
| 4,710,489 | 12/1987 | Meister | 514/18 |
| 4,769,382 | 9/1988 | Dubur et al. | 514/356 |
| 4,818,521 | 4/1989 | Tamabuchi | 424/62 |
| 4,839,159 | 6/1989 | Winter et al. | 424/59 |
| 4,895,727 | 1/1990 | Allen | 424/642 |
| 4,895,840 | 1/1990 | Burke et al. | 424/59 |
| 4,961,926 | 10/1990 | Gabrilove | 424/85.1 |
| 5,008,119 | 4/1991 | Matsubara | 514/18 |
| 5,023,235 | 6/1991 | N'Guyen et al. | 424/59 |
| 5,075,102 | 12/1991 | Hubaud et al. | 424/59 |
| 5,290,809 | 3/1994 | Ippolito et al. | 514/458 |
| 5,306,486 | 4/1994 | McCook et al. | 424/59 |
| 5,409,693 | 4/1995 | Perricone | 424/59 |
| 5,441,726 | 8/1995 | Mitchnick et al. | 424/59 |
| 5,486,360 | 1/1996 | Ballagh et al. | 424/94.4 |
| 5,494,924 | 2/1996 | Cavazza et al. | 514/357 |
| 5,516,507 | 5/1996 | N'Guyen et al. | 424/59 |

*Primary Examiner*—Jyothsna Venkat
*Attorney, Agent, or Firm*—Malcolm B. Wittenbert

[57] ABSTRACT

A composition of glutathione and selenoamino acid in a topical carrier and method of using the composition to reduce and repair x-ray radiation-induced skin damage.

17 Claims, No Drawings

X-RAY INDUCED SKIN DAMAGE PROTECTIVE COMPOSITION

TECHNICAL FIELD OF THE INVENTION

The present invention deals with the combination of several antioxidants employed in a topical carrier as a means of minimizing either early or late radiation-induced skin changes resulting from the use of x-ray radiation in oncology therapy. When tissues are exposed to ionizing radiation, most of the gamma energy supplied by the x-ray source is absorbed by water contained within the cell resulting in the formation of hydrogen and hydroxyl radicals. Certain antioxidants, particularly, glutathione and acetyl-L-carnitine, as well as the element selenium, the co-factor in the enzyme glutathione peroxidase, can be employed in a suitable carrier such as a lotion, cream, spray or gel to protect and treat the overlying skin surface during radiation therapy in specifically dealing with the effects of the hydroxyl, superoxide and other free radicals on biomolecules and lipid membranes.

BACKGROUND OF THE INVENTION

It is well recognized that x-ray radiation is a valuable curative and palliative oncological tool. Radiation therapy is employed for the treatment of many benign and malignant lesions and for organ and bone marrow transplantation modalities.

Although the value of radiation in oncology therapy is universally recognized, the use of high energy radiation in conjunction with chemotherapy is not without its adverse side affects. For example, x-ray radiation has been shown to induce early and/or late radiation-induced skin changes such as skin erythema and ulceration including the severe skin reaction with open blisters, named "moist desquamation" as well as the development of skin cancers.

Up until the 1960's, orthovoltage energies in the range of 150 to 300 kilovolts were used with 100% of the dose delivered to the skin. Doses of x-ray radiation producing skin erythema were used as a quantitative measure as skin reactions were noted to be dose limiting. Today, however, treatment with the electron beam in radiotherapy provides a very high dose to the skin because of rapid dose buildup near the skin surface, compared to earlier megavoltage machines.

It is hypothesized that when tissues are exposed to ionizing radiation, gamma energy is absorbed by water contained within the cells resulting in breakage of the oxygen-hydrogen covalent bonds of the water molecule leaving hydrogen and hydroxyl radicals in situ. It is known that the hydroxyl radical is quite reactive in its interaction with other biomolecules generally thought to be responsible for setting off chain reactions including interactions with the purine and pyrimidine bases of nucleic acids. Many of those who have studied the effects of gamma radiation on the human body believe that radiation-induced cutaneous carcinogenesis may have been initiated by free radical damage. Since radiation often is applied to the human body as a treatment of "deep" lesions such as lung, breast, liver and brain malignancies, it is important to protect the skin from radiation-induced skin damage.

Animals with epithelial tumors have been shown to have increased blood glutathione (GSH) levels. Similarly, higher glutathione levels were detected in groups of humans with disseminated gastric adenocarcinoma and in those with localized or locally advanced skin carcinoma without metastasis. Mean blood GSH levels were 78% and 31% higher, respectively, when compared to control subjects. In blood, most of GSH is present in the red blood cells and may reflect the body's reaction to produce its prime antioxidant, GSH, in response to epithelial malignancies. The rate of generation of GSH within the red blood cells may indicate the body's protective response to reactive species, free radicals, released into plasma by tumors and inflammation.

Antioxidants have been found to inhibit all stages of carcinogenesis whereas other antioxidants are more specific and thus more effective against tumor initiation or promotion and tumor progression. Glutathione and selenium have been shown to play prime roles in protection of carcinogenesis, the latter particularly in skin tumors, when selenium is applied locally as selenomethione or other thiol bonds but also in preventing other cancers, when selenium is taken orally thereby replenishing selenium body stores. Likewise, glutathione, the most abundant tissue thiol and antioxidant, inhibits carcinogenesis, as stated, and indeed when its concentration is suppressed by chemicals so that glutathione levels are significantly lowered, chemical carcinogenesis is enhanced and progression of tumor numbers and tumor size increases. Thus, these studies show the value of glutathione in prevention of tumor formation, making it the ideal antioxidant ingredient along with the other synergistically acting antioxidants in these cosmetic preparations.

The role of intracellular GSH in irradiated cancer cells has been investigated. Reducing the intracellular levels of GSH in tumor cells increases their sensitivity to irradiation or oxidant damage mediated by activated neutrophils or macrophages. Inhibition of GSH synthesis also augments lysis or murine tumor cells by sulfhydryl-reactive anti-neoplastics. Thus, neoplastic cells depleted of their endogenous protective antioxidant, GSH, are more sensitive to radiation damage. Conversely, other studies have shown that increases in intracellular GSH are beneficial. An L-cysteine delivery agent not only enhanced endothelial cell GSH concentration, but also protected these cells in an inverse, linear relationship from damage by endogenous hydrogen peroxide. This preventive role of GSH is of value in treating skin overlying deep areas to be irradiated for cancer but these topical preparations, conversely, are not clinically indicated in the radiotherapy of primary cutaneous neoplasias or malignant skin recurrences.

In the past, attempts to protect the skin from x-ray radiation in oncology therapy has been by a variety of moisturizers and lipid preparations, including aloe vera and mineral oil. However, such compositions have enjoyed little or no success in preventing or healing radiation skin damage.

It is thus an object of the present invention to provide a composition useful in minimizing early as well as late radiation-induced skin changes.

It is yet a further object of the present invention to provide in the form of a topical carrier, certain antioxidants which are effective in reducing radiation-induced cutaneous carcinogenesis which is initiated by the formation of free radicals.

These and further objects will be more readily apparent when considering the following disclosure and appended claims.

SUMMARY OF THE INVENTION

The present invention deals with a composition and method for reducing the effects of x-rays in inducing skin damage. The composition comprises an effective amount of a glutathione and selenoamino acid as the co-factor of glutathione peroxidase. The combination can be in the form of a lotion, cream, gel, spray or emulsion and can also include the further antioxidants acetyl-1-carnitine and superoxide dismutase as well as secondary components to be discussed hereinafter.

DETAILED DESCRIPTION OF THE INVENTION

As previously noted, the present invention deals with the glutathione (GSH), in combination with a selenium compound used topically to act as free radical scavengers reducing radiation-induced skin changes. It is proposed that the described active ingredients be employed in topical compositions. Topical carriers are employed which should be both non-irritating to the skin and which are suitable for delivering the active components to the skin. Further, suitable topical carriers should be those which do not inhibit the antioxidant activity of the active ingredients thus reducing the efficiency of the composition for protecting the skin from the effects of x-ray radiation. Further, such carriers must be of sufficiently high purity and sufficiently low toxicity to render them suitable for chronic topical administration to the skin.

Without being bound to any particular theory, it is noted that reduced glutathione is employed in protecting cells and aerobic organisms against oxidative stress by itself being oxidized. Thus, glutathione must act in combination with other enzyme systems in order to be reduced so that it may renew its role as a free radical scavenger. GSH functions also coordinately with the enzyme glutathione peroxidase to break down hydrogen peroxide and lipid hydroperoxides. Glutathione peroxidase in the body requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew.

It is further contemplated that the present composition, as a preferred embodiment, include acetyl-1-carnitine. This latter component further participates in protecting cells against lipid peroxidation by locally increasing the amount of antioxidizing agents of GSH and ubiquinol. L-carnitine, also known as gamma trimethylamino-beta hydroxybutyrate or Vitamin Bt occurs naturally in the body. It is a normal endogenous intermediary metabolite which has been identified in all mammalian cells and in blood and urine. It has the function of transporting fatty acids and other acidulated compounds across inner mitochondrial membranes and of maintaining the acyl CoA/free CoA ratio between the mitochondria and the cytosol of the cells. Acetyl-1-carnitine is the acetyl derivative of 1-carnitine and is also a naturally occurring substance in the body as it provides a transport mechanism for the acetyl groups created by the beta oxidation of fatty acids while concomitantly regenerating acetyl co-enzymes in the cytosol of the cell.

Of interest herein, acetyl-1-carnitine has been shown to have a scavenging effect on the free superoxide anion. This antioxidant activity coupled by acetyl-1-carnitine's effect of inducing an increase in reduced glutathione and reduced ubiquinone levels provides a stabilizing effect on membranes by decreasing membrane lipid peroxidation. The skin is a highly vascular organ, extracellularly very rich in polyunsaturated fatty acids. The irradiated skin with its exposure to atmospheric oxygen is most prone to process of lipid peroxidation and thus skin may be readily damaged by radiation therapy. Thus, reduced glutathione and acetyl-1-carnitine in a topical preparation will act somewhat synergistically; the former as a reparative antioxidant which itself becomes oxidized and better able to be regenerated locally in its reduced form by the metabolic functions of acetyl-1-carnitine and by acetyl-1-carnitine's ability to enhance mitochondrial energy production. This is accomplished by its actions on lipid metabolism and by the resulting increase in cytochrome oxidase, the final enzyme in the cellular respiratory chain.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxidase. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydro peroxides.

As noted previously, the active ingredients described above can be incorporated in any suitable pharmacologically acceptable carrier which is suitable for topical administration to the human skin. As such, the pharmacologically acceptable carrier must be of sufficient purity and have sufficiently low toxicity to render it suitable for administration to a human noting that, typically, the carrier can represent up to 99.99% and typically from at least approximately 80% of the total composition.

Typical compositions for use herein include a wide variety of physical forms. These include, but are not limited to, solutions, lotions, creams, oils, gels, sticks, sprays, ointments and pastes. Generally, such carrier systems can be described as being solutions, emulsions, gels and solids.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated by reference.

Alternatively, the present composition can be formulated as a lotion containing from about 0.01% to 10% of the above described active ingredients. Further, the product can be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that as one embodiment, the active ingredients described above be used as a lotion or cream emulsion of the oil-in-water type or as a water-in-oil type, both of which being extremely well known in the cosmetic field. Multiphase emulsions such as the water-in-oil type is disclosed in U.S. Pat. No. 4,254,105, the disclosure of which is incorporated herein by reference.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

EXAMPLE 1

A composition containing the following ingredients was prepared in making the gel suitable for use in protecting skin from x-ray induced damage:

| Ingredient | Percentage |
| --- | --- |
| Water | 90.93 |
| Seaweed | 2.09 |
| Hydroxyethylcellulose | 1.32 |
| Cetiol HE | 1.3 |
| Vitamin B-5 | 0.93 |
| Green Tea | 0.7 |
| Sodium Hydroxymethylglycinate | 0.54 |
| PEG 20 Crovol A-40 | 0.45 |
| Honey | 0.4 |
| NaPCA | 0.26 |
| Sodium Lactate | 0.22 |
| Pseudo Collagen | 0.2 |
| Sodium Hyaluronate | 0.15 |
| Glutathione | 0.15 |
| Vitamin B Complex | 0.12 |
| Carbomer | 0.07 |
| Zinc Glycopeptide | 0.05 |
| Selenomethionine | 0.03 |
| Acetyl L Carnitine Hydrochloride | 0.03 |
| Superoxide Dismutase | 0.03 |
| Lecithin | 0.03 |

In preparation, water and hydroxyethylcellulose were combined and heated to 55° C. under continual agitation. After thickening, carbomer and cetiol HE were added to the thickened gum whereupon the composition was cooled to 30° C. at which time the remaining components listed above were added.

EXAMPLE 2

A composition containing the following ingredients was prepared in making the solution suitable for use in protecting skin from x-ray induced damage:

| Ingredient | Percentage |
| --- | --- |
| Water | 92 |
| Seaweed | 2.09 |
| Hydroxyethylcellulose | 0.32 |
| Cetiol HE | 1.3 |
| Vitamin B-5 | 0.93 |
| Green tea | 0.7 |
| NA Hydroxyethylglycinate | 0.54 |
| PEG 20 Crovol A-40 | 0.45 |

-continued

| Ingredient | Percentage |
| --- | --- |
| Honey | 0.4 |
| NaPCA | 0.26 |
| Sodium Lactate | 0.22 |
| Pseudo Collagen | 0.2 |
| Sodium Hyaluronate | 0.15 |
| Glutathione | 0.15 |
| Vitamin B Complex | 0.12 |
| Yeast Mineral Glycopeptide | 0.05 |
| Selenomethionine | 0.03 |
| Acetyl L Carnitine Hydrochloride | 0.03 |
| Superoxide Dismutase | 0.03 |
| Lecithin | 0.03 |

Water and hydroxyethylcellulose were combined at 55° C. under continual stirring. After thickening, cetiol HE was added to the gum and, subsequently, NA hydroxyethylglycinate was mixed into the thickened gel and the composition then cooled to 30° C. whereupon the remaining ingredients were added.

EXAMPLE 3

A composition containing the following ingredients was prepared in making the cream suitable for use in protecting skin from x-ray induced damage:

A first water phase was prepared by combining water (73.002%) EDTA (0.08%) and gum (0.067%) by charging an appropriate vessel with distilled water and agitating the water to disperse the EDTA whereupon the gum was added and the solution gently heated to 65° C. A second water phase was prepared including water (2.80%), niacinamide (0.09%) and Carbomer (0.067%) by adding the niacinamide to the second water phase with stirring until dissolved. The carbomer was then added and the solution allowed to thicken and totally dissolve. The second water phase was then added to the first. At this time, glycerol cocoate (0.105%) was added and the following ingredients separately were combined and heated to 75° C. whereupon the combination was added to the water phase en mass:

| Ingredient | Percentage |
| --- | --- |
| Sesame oil | 1.52% |
| Canola oil | 8.65% |
| Stearic acid | 3.209% |
| Cetyl Alcohol | 2.114% |
| Cocoa butter | .56% |
| Glyceryl Stearate & PEG 100 Stearate | .379% |
| 556 Cosmetic grade fluid | .899% |
| PEG 10 Soya Sterol | .12% |
| Caschem 200 | .12% |
| Squalane oil | .095% |
| Arnica oil | .096% |
| Calendula oil | .096% |

Throughout this process, the aqueous phase was maintained at a temperature of 60°–65° C. The various ingredients were mixed for approximately ten minutes whereupon triethanolamine (0.305%) was added and mixing continued for 2–3 minutes whereupon the composition was cooled to 50° C. At this time, the following ingredients were further added:

| | |
|---|---|
| Vitamin B5 | 0.714% |
| Vitamin C oil mix | 0.284% |
| Lecithin | 0.054% |
| Sodium PCA | 0.16% |

The temperature was reduced to 45° C. and the following degrees next added:

| | |
|---|---|
| Seaweed | 2.13% |
| Vitamin B complex | 0.11% |
| Yeast Mineral Glycopeptide | 0.048% |
| Sodium Lactate | 0.035% |
| Glutathione | 0.15% |
| Selenomethionine | 0.03% |
| Acetyl L Carnitine | 0.03% |
| Superoxide Dismutase | 0.03% |
| NA Hydroxymethylglycinate | 0.07% |

Temperature of the composition was further reduced to 30° C. at which time the following ingredients were added:

| | |
|---|---|
| Carrot oil | 0.0392% |
| Sodium Hyaluronate | 0.16% |
| Green tea | 0.03% |
| Vitamin A and D3 | 0.06% |
| Echinacea | 0.047% |
| Honey | 0.0452% |
| Lactic acid | 0.018% |
| Germaben II ® (Propyleneglycol, diazolidinyl urea, methyl paraben, propyl paraben) | 0.99% |
| Vitamin B complex | 0.11% |

EXAMPLE 4

A composition containing the following ingredients was prepared in making the aerosol composition suitable for use in protecting skin from x-ray induced damage:

| Ingredient | Percentage |
|---|---|
| Water | 1 |
| Vitamin B5 | 1 |
| Vitamin C (ascorbic acid) | 0.16 |
| Glycerin | 1 |
| Isopropyl myrystate | 1 |
| Dipropylene glycol | 5 |
| Alcohol | 90 |
| Glutathione | 0.15 |
| Selenomethionine | 0.03 |
| Acetyl L carnitine hydrochloride | 0.03 |
| Superoxide dismutase | 0.03 |
| Green tea | 0.6 |

In preparation, water was added to vitamin B5 and vitamin C (ascorbic acid) in the percentages indicated. The remaining ingredients were separately mixed and the final combination of ingredients thereupon completed.

EXAMPLE 5

A composition containing the following ingredients was prepared in making the ointment suitable for use in protecting skin from x-ray induced damage:

| Ingredient | Percentage |
|---|---|
| Propylene glycol | 1 |
| Vitamin B5 | 1 |
| Cholesterol | 2.8 |
| Stearyl alcohol | 2.9 |
| White wax | 8 |
| White petroleum | 83.46 |
| Glutathione | 0.15 |
| Selenomethionine | 0.03 |
| Acetyl L carnitine hydrochloride | 0.03 |
| Superoxide dismutase | 0.03 |
| Green tea | 0.6 |

As preparation, propylene glycol and vitamin B5 were separately mixed while stearyl alcohol, white wax and white petroleum were separately mixed. After mixing the subcomponents, the remaining ingredients were added and the combination completed.

As noted from the above, although applicant can employ commercially available selenium containing selenoamino acids such as L-selenomethionine such as those described in U.S. Pat. No. 4,865,840, the disclosure of which is incorporated by reference herein, applicant can also use as its selenium source, a selenium yeast extract. The proposed preparations may be used alone or in combination with essential mineral glycopeptides. These compounds are elaborated in the laboratory by feeding the putative metal ions to living yeast cultures by standard microbiologic techniques. The yeast organisms are able to incorporate the minerals as complexes within the cellular glycoproteins.

These complexes are mineral yeast extracts and are commercially available from suppliers such as Brooks Industries, Plainfield, N.J., Pharmachem, South Hackensack, N.J. and Triarco, Patterson, N.J. The mineral-yeast extracts include the following, alone, or in combination with calcium, copper, germanium, iron, manganese, magnesium, selenium, silicon and zinc. These glycopeptides containing one or more of the aforementioned minerals have been shown to possess less toxicity and increased penetration into the skin. Mineral amino acid chelates may also be used and are widely available from commercial suppliers.

The mineral selenium yeast extract, as noted above, is prepared similarly by feeding the selenium to living yeast cultures. Preparations of selenium yeast extract as SE-glycopeptide, are available as clear, low odor, filtered solutions. These have been shown to have moisturizing, toning and skin revitalizing properties. The selenium yeast extract penetrates into the skin and the selenium participates in its usual metabolic activities, including acting as a co-factor for the enzyme glutathione peroxidase. (See selenium OP cit). The addition of selenium yeast extract to these topical preparations enhances these as it synergizes with reduced glutathione and other antioxidants.

As further noted from several of the examples, the present invention further contemplates the use of additional optional expedients, for example, superoxide dismutase (SOD). SOD is a ubiquitous cellular enzyme whose main function is in protecting cells against oxidative stress. Superoxide dismutases are a family of cytosolic metaloenzymes which specifically remove free oxygen radical ($O_2^-$). There are three distinct forms of SOD, namely, CUZN SOD, MN SOD and extracellular SOD (EC-SOD) which is a copper enzyme located on endothelial cell surfaces. The differences in the SODs is in their aminoacid sequences as well as location at their active sites of the transition metals. It is hypothesized that the enzyme SOD, along with glutathione peroxidase and its selenium cofactor are effective preventive antioxidants because they eliminate molecules involved in the initiation of free radical reactions. SOD also protects intracellular reduced glutathione against radical mediated chain oxidation as the combination of SOD and reduced glutathione prevents redox cycling reactions.

It is also contemplated that, as a further optional expedient that the present composition contain from approximately 0.01% to 10% Japanese green tea. Chemically, extracts of Japanese green tea have been analyzed and characterized. Active ingredients include caffeine, theobromine, theophylline and xanthines which, together, have been shown to reduce irritation of the skin, including that caused by various alpha hydroxy acids and other ingredients in cosmetics, thus making green tea an important supplement in topical cosmetic and dermatological preparations. Green tea also contains potent polyphenols, catechin compounds which effectively act as antioxidant agents to scavenge for radicals. The main catechin constituent of green tea is (−)epigallo catechin gallate (EGCG) which has been shown to possess anti carcinogenic properties, including in experimental animals, as a cancer chemopreventive agent, by reducing too the specific binding to the cell receptor. It has also been shown that EGCG inhibits hydrogen peroxide formation by human leukocytes, the first cell in the inflammatory cellular response to injury. Thus, categorically, EGCG suppresses oxyradical formation in vivo and so is of value to function synergistically as an exogenous antioxidant in these topical preparations with the active ingredients comprised of endogenous antioxidants.

In a preferred embodiment, the compositions of the present may be enhanced by the addition of zinc salts. Zinc may function by its healing properties on wounds, particularly as zinc oxide, and also to render the present preparations odorless, presumably by removing traces of hydrogen sulfide, which could emanate from sulfur groups used in these preparations. Zinc may also be administered as one of the trace metals prepared in yeast extracts as mineral (zinc) glycopeptides.

Compositions preferably comprise from about 0.001% to about 8% of a zinc salt, more preferably from about 0.01% to about 4%, more preferably still from about 0.1% to about 0.5%.

Zinc, the second most abundant trace metal in the human body and present in all living cells and body secretions, was identified as a trace metal by Ravlin in 1869. 25% of total body zinc content is found in the skin mainly as zinc metaloenzymes. For over 3000 years, zinc in the form of zinc oxide or calamine, has been used in the treatment of wounds. Zinc is still used in castor oil for treatment of diaper rash and in a vast number of zincated bandages, dressings and creams.

It has more recently been shown that zinc metaloenzymes in the skin have a prominent role in the reconstruction of the wound matrix. Zinc, along with copper is necessary for cross-linking of collagen fibers in the skin repair process. Although zinc probably plays a role in all stages of healing, zinc concentrations increase at the margins of the wound during the formation of granulation tissue, re-epithelialization and normalization periods, whereas cutaneous calcium requirements are greater during hemostasis and inflammation. The concentrations of zinc in the margins of the wound during repair are 15–20% higher than in contiguous intact skin and are provided from zinc in blood. Since zinc thus is of value in the skin healing process as shown in experimental animals and in clinical studies with zinc oxide, the addition of zinc as an ingredient to these preparations will promote the healing of radiation induced skin damage. The form of presentation of the zinc-aqueous gel or paste, cream in amphillic vehicle, lotion or emollient will influence the amount of zinc that is absorbed by the skin and thereby affect the wound's micro-environment.

Like the same tissue and cellular damage produced by radiation, oxidant by-products of normal metabolism cause extensive damage, as stated, to cells, membranes, DNA, proteins and lipids. Anti-oxidants, as endogenous enzymes and scavenger molecules, like GSH, act as defenses against this oxidant damage. Other exogenous molecules such as the ascorbates and tocopherols also assist in these defense mechanisms acting synergistically with glutathione to effect preventive and reparative mechanisms to oxyradical damage.

Vitamins, as those included in these preparations, are naturally derived from dietary fruits and vegetables, particularly ascorbates and caretenoids, but also are sources of tocopherols. Natural and synthetic vitamins may be taken as supplements in various foods and beverages or as pharmaceutic preparations of multivitamins and minerals. These preparations provide these vitamins in sufficient concentrations to exert locally their physiologic and pharmacologic properties.

Vitamin E, particularly in its alpha-tocopherol moiety, has been employed to inhibit oxidation of oils and fats in foods, cosmetic preparations and drugs. Vitamin E is not only an anti-oxidant but also has anti-inflammatory properties. In skin, vitamin E levels are present in dermis and epidermis, but are depleted by radiation and ultraviolet light, thus their importance too in providing these to act in vivo as antioxidants, elevating their tissue levels and protecting skin cells. Vitamin E moisturizes and enhances its smoothness. It is soothing and also participates in wound healing.

Cell membranes and plasma lipoproteins contain alpha tocopherol, which is a lipid soluble molecule that functions as a chain breaking (reparative) anti-oxidant. An —OH attached to the hydrophobic structure of tocopherol easily releases its hydrogen atom, so that peroxyl and alkoxyl free radicals generated during lipid peroxidation then may combine with this anti-oxidant instead of with adjacent fatty acid side chains, thereby terminating this chain reaction during lipid peroxidation. Experimental evidence shows that the tocopherol radical migrates to the membrane surface. It is then reconverted to alpha tocopherol by its reaction with ascorbic acid (vitamin C). Thus vitamins E and C are synergistic and minimize the toxic effects on lipid peroxidation in membranes and lipoproteins. Moreover, glutathione and selenium also act synergistically with vitamin E, the former GSH, by regenerating alpha tocopherol from its tocopherol radical form. Vitamins C and E, selenium and glutathione, in experimental animals, have been shown to work together as anti-oxidants in inhibiting skin tumor promotion and/or tumor progression. Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against radiation, including ultra violet rays.

Ascorbates can repair oxidizing radicals directly and are therefore characterized as chain-breaking anti-oxidants. Through this mechanism, ascorbic acid and also tocopherols, have also been shown to reduce significantly chemically induced tumor formation in experimental animals.

Vitamin C, a water soluble exogenous small molecule anti-oxidant, is located in aqueous phases of cells while, as noted, vitamin E is in the lipid portion of membranes. Together they protect lipids and lipid structures against peroxidation. Vitamin C repairs the tocopheroxyl radical and permits that molecule to function again as a tocopherol free radical chain-breaking anti-oxidant. The ascorbate free radical produced in this reaction with tocopherol can be removed from the tissues by a dismutation reaction. The dehydroascorbate and the ascorbate radical can then be removed by enzyme systems that use NADH or NADPH as sources of reducing molecules. Thereby, ascorbate is recycled to protect again the process of lipid peroxidation by its synergistic function with vitamin E.

Thus, these topical preparations will, in their preferred form, contain mixtures of vitamins C and E to enhance locally the anti-oxidant activities of the active ingredients, particularly in their function as chain-breaking anti-oxidants in lipid peroxidation.

The present invention also contemplates, as an optional expedient, the inclusion of vitamin A. Vitamin A, retinol, is also known as the anti-xerophthalmic vitamin, occurs only in animal organisms and is not found in plants. It is usually extracted from liver oils, mainly in its esterified forms but may also be synthesized in the laboratory. The liver converts carotenoids, particularly beta-carotene, into vitamin A. Dihydroretinol, vitamin A2, is the visual pigment. Vitamin A and its derivatives, particularly vitamin A palmitate (retinyl palmitate) may be used in these preparations, more in concentrations from 0.001 to 1% but more preferably from 0.005 to 0.09%. Retinyl palmitate, a common ingredient in cosmetics, has been shown to penetrate the skin and like vitamin A is essential for normal skin, nail and hair development. It increases skin elasticity and promotes thickening of the epidermis and dermis. In experimental animals, vitamin A has been shown to reverse changes of photodamage (radiation). An analog of vitamin A, retinoic acid, has also been shown to reverse changes of photoaging in humans.

Beta-carotene, which is pro-vitamin A, is found in many plants and is a nutrition source and the main coloring matter in carrots and egg yolks. B-carotene is used in cosmetics as a coloring agent and also as a source to the body of vitamin A. Carotene, like vitamin A, may be absorbed by the skin. Carotenoids, including beta-carotene, are small molecule dietary and topical anti-oxidants which may have also anticarcinogenic properties and act as defenses against degenerative diseases in the body. Most carotenoids have anti-oxidant activities particularly against the free oxygen radical species. Carrot oil is rich in vitamin A and carotenoids and may be used in these preparations in a concentration between 0.001% and 1% as a source of these molecules. It is a light yellow essential oil derived from seeds of carrots and has no known toxicity. Carrot seed extract, may also be used and is derived from the seed of daucus carota sativa.

Squalene, obtained from shark liver oil, may be used also in concentrations of 0.001 to 0.10%. It is a lubricant and has been shown to possess bactericidal properties.

A further expedient is the use of dexpanthenol (panthenol, pro-vitamin B5) which is part of the B complex and precursor of pantothenic acid (vitamin B5). Dexpanthenol is a nutritional and topical factor as a source of vitamin B5, which is present in all cells and is a constituent of co-enzyme A. The activated acetates from acetylation reactions (Krebs cycle) are essential in the synthesis or lipids and proteins and the linkages between these two and carbohydrates. Dexpanthenol is used in these preparations for it is a quick and deep penetrating moisturizer and promotes normal skin keratinization. It has been shown to stimulate fibroblast proliferation and also to promote tissue repair and wound healing.

In accordance with the present invention, as a further preferred embodiment, one or more cell growth stimulating compounds in suitable amounts effective for stimulating the growth of cells which encompass, or surround, and are injured or are responsible for healing wounds will be incorporated in the present preparations of creams, lotions or gels.

Cells subjected to oxidative stress may severely affect cellular function and cause damage to membrane lipids, to cytoskeletal structure and to DNA. Free radical damage to DNA has been measured as formation of single-strand breaks, double-strand breaks and chromosomal aberrations. Cells exposed to ionizing radiation and cigarette smoke have been demonstrated to have an increased intracellular DNA damage. Tissues exposed to ionizing radiation result in the breakage of water molecules, with consequent production of the potent hydroxyl radical. This reactive free species sets up a variety of deleterious biochemical chain reactions, including interactions with purine and pyrimidine bases, thereby affecting DNA. Similarly, in clinical conditions, including skin injury due to solar radiation, the aging process, radiation injury, and radiotherapy, oxygen free radicals have been shown to be mutagenic and pathogenic of DNA structure and thus DNA changes are related to increased frequency of associated malignancies, including the three types of skin cancer, squamous and basal cell carcinomas and malignant melanoma.

In this regard, the present invention will employ cell growth stimulating compounds or factors which have been described as natural or exogenous compounds which have a stimulating effect on the elaboration and growth of specific cell lines. These include anabolic growth hormones, as human growth hormone and thyroid stimulating hormone, or on specific cell lines as granulocytes, platelets or erythrocytes. Specifically in regard to promoting epidermal growth, such as in skin tissue repair or wound healing, various factors have been identified as growth factors, including epithelial (epidermal) growth factor (EGF), fibroblast growth factor (FGF), tissue respiratory factor (TRF), transforming growth factor (TGF) and insulin-like growth factor (IGF).

TRF is a live yeast cell derivative which has been used in over the counter pharmaceutical preparations since patented in the 1940's and more recently as an ingredient in cosmetics. It is commercially available (Brooks Industries Biodynes-TRF, South Plainfield, N.J.) and purported to be a powerful internal moisturizer which refreshes dry and infirm skin. TRF was first used as an anti-hemorrhoidal product (Preparation H, Whitehall Laboratories). TRF is composed of low molecular weight glycosidic/peptide fractions with a ratio of 1:3. The residual glycopeptide linkages are through the amino acid asparagine residues. Because TRF is prepared from live yeast cell derivatives, additional trace quantities of coenzymes, vitamins, amino acids, and mineral characteristic of yeast, are available in these factors, which enhance the therapeutic capabilities of the TRF in these pharmaceutic/cosmetic preparations.

TRF has a maximum absorbance of 13.0–20-0; ultraviolet spectrophotometer of a 1% TRF filtered solution reads at 256–258NM. It is available as a water soluble material for gels, emulsions, lotions and creams. TRF has been shown to promote wound healing through its ability to increase fibroblast synthesis of collagen and elastin, resulting in smoothing of the skin. TRF's internal moisturizing effect is accomplished by increasing uptake of moisture by nascent protein and increasing oxygen utilization in the skin. TRF has been used in the treatment of sunburned skin and has been preferred for decreasing pain and discomfort of sunburn damaged skin when compared to a topical post-sun product containing the local anesthetic benzocaine. Thus, TRF, as other growth factors, may be used in combination with the presently proposed anti-oxidant preparations as a preventive and prophylactic agent to photodamaged, irradiated or inflamed skin of various etiologies.

As a further optional component for use herein is epidermal growth factor (EGF) which is a commercially available endogenous substance for the development and maintenance of the epidermis and dermis. EGF is a protein that catalyzes the cutaneous healing process by promoting epidermal and epithelial cells to divide and grow. It induces mitoses, so that skin constantly produces and uses EGF, particularly when skin is damaged, such as in radiation and after surgery, and trauma for both healing and reduction of scar and keloid formulation. When applied topically, EGF generates and replaces cells. EGF also promotes synthesis of proteins, accumulation of collagen and formation of blood vessels. Following radiation, sunlight injury and during the aging process, topical application of EGF replaces the existing low levels of growth factors to achieve improvement in the quality of the skin, thereby reducing sagging skin and wrinkles. The anti-oxidants protect and repair damaged skin from free radicals while the growth factors to be used in combinations will promote epidermal cell renewal and thus ensue in repair of affected tissues. Epidermal growth factor is a 53 amino acid polypeptide which stimulates messenger RNA, DNA and protein synthesis. In vitro it stimulates keratinocyte division and in vivo epidermal regeneration.

After cutaneous injury, residual epithelial cells proliferate as a response to injury in an organized fashion to regenerate an intact epidermis. Superficial wounds which do not result in total skin loss but retain at least a portion of the dermal layer, heal primarily by this process of epidermal regeneration. Epidermal growth factor induces replacement of cells by inducing mitosis. Many experiments, animal and human studies, have positively shown the beneficial effect of EGF in the process of wound repair. These clinical situations include partial thickness burn, skin graft donor sites and chronic skin ulcers. It is also of use in healing radiation skin burns, surgical scars and in the repair process of cosmetic surgeries and cutaneous chemical peels.

A suitable composition for use of the present invention as a reparative cream is as follows:

| Ingredient | Percentage |
|---|---|
| Water | 59.751 |
| Gum (hydroxyethylcellulose) | .8 |
| EDTA | .09 |
| PEG/Glycerol Cocoate | .14 |
| Sesame Oil | 8.73 |
| Canola Oil | 5.98 |
| Squalane Oil | .95 |
| Cetearyl Alcohol & Ceteareth 20 | .215 |
| Cetearyl Alcohol & Polysorbate 60 | .254 |
| Stearic Acid | 3.099 |
| Cetyl Alcohol | 2.348 |
| Caschem 200 | 1.787 |
| 556 Cosmetic Grade Fluid | 1.062 |
| PEG 10 Soya Sterol | .122 |

-continued

| Ingredient | Percentage |
|---|---|
| Cocoa Butter | .84 |
| Triethanolamine 99% | .29 |
| Lecithin | .02 |
| Sodium PCA | .27 |
| Seaweed | 5.54 |
| Sodium Hyaluronate | .193 |
| Marigold | .2 |
| Sodium Lactate | .038 |
| Lactic Acid | .018 |
| Honey | .452 |
| Vitamin B5 | 1.038 |
| Vitamin B Complex | .215 |
| Vitamin C and Oil Mix | 1.226 |
| Psuedo Collagen | .93 |
| Vitamins A and D3 | .7 |
| Carrot Oil | .09 |
| Glycopeptide Zinc | .17 |
| Serum Albumin | .857 |
| Germaben 11 ® (propyleneglycol, diazolidinyl urea, methyl paraben, propyl paraben | 1.065 |
| Glutathione | .03 |
| Selenomethionine | .03 |
| Acetyl L Carnitine HCL | .03 |
| Green Tea | .06 |
| Superoxide Dismutase | .03 |
| Carbomer | .09 |
| Epidermal Growth Factor | .25 |

I claim:

1. A composition for protection from x-ray induced skin damage comprising L-selenomethionine and glutathione to reduce x-ray radiation induced skin damage in a suitable carrier for topical application wherein said L-selenomethionine is present in the carrier in a concentration of at least 0.01% by weight and said glutathione is present in the carrier in a concentration of at least 0.03% by weight based upon the weight of the composition.

2. The composition of claim 1 wherein said carrier is in the form of a member selected from the group consisting of a lotion, cream, gel and emulsion.

3. The composition of claim 1 further comprising acetyl-l-carnitine.

4. The composition of claim 1 further comprising Japanese green tea.

5. The composition of claim 3 wherein said acetyl-l-carnitine is present in the carrier in a concentration of at least approximately 0.01% by weight based upon the weight of the composition.

6. The composition of claim 1 further comprising superoxide dismutase.

7. The composition of claim 6 wherein said superoxide dismutase is present in the carrier in a concentration of at least approximately 0.01% by weight based upon the weight of the composition.

8. The composition of claim 1 further comprising at least one member selected from the group consisting of vitamin E, vitamin C, vitamin A, and vitamin B5.

9. The composition of claim 1 further comprising approximately 0.001 to 1.0% squalene by weight based upon the weight of the total composition.

10. The composition of claim 1 further comprising zinc in an amount between approximately 0.001% to 8.0% by weight based upon the weight of the total composition.

11. A method of protecting skin from x-ray-induced skin damage comprising topically applying to the skin an amount of a composition of a L-selenomethionine and glutathione effective to provide protection from x-ray radiation-induced skin damage wherein said L-selenomethionine is present in the carrier in a concentration of at least 0.01% by weight and said glutathione is present in the carrier in a concentration of at least 0.03% by weight based upon the weight of the composition.

12. The method of claim 11 wherein said carrier is in the form of a member selected from the group consisting of a lotion, cream, gel and emulsion.

13. The method of claim 11 further comprising acetyl-l-carnitine.

14. The method of claim 11 further comprising Japanese green tea.

15. The method of claim 13 wherein said acetyl-l-carnitine is present in the carrier in a concentration of at least approximately 0.001% by weight based upon the weight of the total composition.

16. The method of claim 11 further comprising superoxide dismutase.

17. The method of claim 16 wherein said superoxide dismutase is present in the carrier in a concentration of at least approximately 0.001% by weight based upon the weight of the total composition.

* * * * *